(12) United States Patent
Lim et al.

(10) Patent No.: US 7,798,993 B2
(45) Date of Patent: Sep. 21, 2010

(54) SINGLE USE SYRINGE

(75) Inventors: Kiang Heng Lim, Singapore (SG); Steven Lau, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 11/196,699

(22) Filed: Aug. 3, 2005

(65) Prior Publication Data

US 2006/0178625 A1 Aug. 10, 2006

Related U.S. Application Data

(63) Continuation-in-part of application No. 10/835,848, filed on Apr. 30, 2004, now abandoned, which is a continuation of application No. 10/256,607, filed on Sep. 27, 2002, now abandoned, and a continuation-in-part of application No. 10/706,795, filed on Nov. 12, 2003, now abandoned.

(51) Int. Cl.
*A61M 5/00* (2006.01)
*A61M 5/315* (2006.01)

(52) U.S. Cl. .................. 604/110; 604/228; 604/218

(58) Field of Classification Search .............. 604/218, 604/221, 228, 110, 187, 181, 905, 235
See application file for complete search history.

(56) References Cited

U.S. PATENT DOCUMENTS

| | | | |
|---|---|---|---|
| 1,742,497 A | 1/1930 | Dickinson | |
| 1,793,068 A | 2/1931 | Dickinson | |
| 2,158,593 A | 5/1939 | Scrimgeour | |
| 2,902,995 A | 9/1959 | Loper | |
| 3,179,107 A | 4/1965 | Clark | |
| 3,234,944 A | 2/1966 | Stevens et al. | |
| 3,301,256 A | 1/1967 | Cowley | |
| 3,320,954 A | 5/1967 | Cowley et al. | |
| 3,331,538 A | 7/1967 | Higgins | |
| 3,469,581 A | 9/1969 | Burke | |
| 3,491,757 A | 1/1970 | Arce | |
| 3,542,024 A | 11/1970 | Burke | |
| 3,712,302 A | 1/1973 | Burke et al. | |
| 4,022,191 A | 5/1977 | Jamshidi | |

(Continued)

FOREIGN PATENT DOCUMENTS

DE 2939180 C2 12/1989

(Continued)

OTHER PUBLICATIONS

PCT International Search Report in PCT/US2006/030076, (Feb. 5, 2008), 7 pgs.

(Continued)

*Primary Examiner*—Nicholas D Lucchesi
*Assistant Examiner*—Quynh-Nhu H Vu
(74) *Attorney, Agent, or Firm*—Diehl Servilla LLC

(57) ABSTRACT

A syringe including a plunger rod assembly including a proximal portion a distal portion with a stopper for expelling fluids from the syringe and a breakable connection between the proximal portion and the distal portion is disclosed. An impulse reduction system, which may be an elastic element or braking surfaces, reduces the contact impulse imparted by the proximal portion upon the distal portion when the connection between the distal portion and proximal portion breaks is also disclosed.

13 Claims, 7 Drawing Sheets

U.S. PATENT DOCUMENTS

| | | | | |
|---|---|---|---|---|
| 4,027,669 A | | 6/1977 | Johnston et al. | |
| 4,215,701 A | | 8/1980 | Raitto | |
| 4,245,654 A | | 1/1981 | Raitto | |
| 4,430,080 A | | 2/1984 | Pasquini et al. | |
| 4,676,530 A | | 6/1987 | Nordgren et al. | |
| 4,699,614 A | | 10/1987 | Glazier | |
| 4,720,285 A | | 1/1988 | Pickhard | |
| 4,775,363 A | | 10/1988 | Sandsdalen | |
| 4,775,364 A | | 10/1988 | Alles | |
| 4,787,891 A | * | 11/1988 | Levin et al. | 604/136 |
| 4,863,427 A | | 9/1989 | Cocchi | |
| 4,874,384 A | | 10/1989 | Nunez | |
| 4,883,466 A | | 11/1989 | Glazier | |
| 4,915,692 A | | 4/1990 | Verlier | |
| 4,923,443 A | | 5/1990 | Greenwood et al. | |
| 4,950,240 A | | 8/1990 | Greenwood et al. | |
| 4,973,308 A | | 11/1990 | Borras et al. | |
| 4,973,309 A | | 11/1990 | Sultan | |
| 5,000,735 A | | 3/1991 | Whelan | |
| 5,004,450 A | | 4/1991 | Ide | |
| 5,047,017 A | | 9/1991 | Koska | |
| 5,059,172 A | | 10/1991 | Sutherland et al. | |
| 5,067,942 A | | 11/1991 | Jaffe et al. | |
| 5,069,225 A | | 12/1991 | Okamura | |
| 5,078,686 A | | 1/1992 | Bates | |
| 5,085,638 A | | 2/1992 | Farbstein et al. | |
| 5,149,323 A | | 9/1992 | Colonna | |
| 5,158,550 A | | 10/1992 | Scholl, Jr. | |
| 5,163,908 A | | 11/1992 | Lambert | |
| 5,181,912 A | | 1/1993 | Hammet | |
| 5,201,709 A | | 4/1993 | Capra | |
| 5,205,833 A | | 4/1993 | Harsh et al. | |
| 5,215,524 A | | 6/1993 | Vallelunga et al. | |
| 5,221,267 A | | 6/1993 | Folden | |
| 5,226,882 A | | 7/1993 | Bates | |
| 5,242,401 A | | 9/1993 | Colsky | |
| 5,248,299 A | | 9/1993 | Ota | |
| 5,269,760 A | | 12/1993 | Bina | |
| 5,336,200 A | | 8/1994 | Streck et al. | |
| 5,344,405 A | * | 9/1994 | Richards | 604/110 |
| 5,352,203 A | | 10/1994 | Vallelunga et al. | |
| 5,383,857 A | | 1/1995 | Levitov | |
| 5,389,075 A | | 2/1995 | Vladimirsky | |
| 5,423,756 A | | 6/1995 | van der Merwe | |
| 5,489,272 A | | 2/1996 | Wirtz | |
| 5,527,286 A | | 6/1996 | Lekhgolts et al. | |
| 5,605,544 A | | 2/1997 | Tsao | |
| 5,643,211 A | * | 7/1997 | Sadowski et al. | 604/110 |
| 5,697,917 A | * | 12/1997 | Sadowski et al. | 604/218 |
| 5,738,655 A | | 4/1998 | Vallelunga et al. | |
| 5,769,822 A | | 6/1998 | McGary et al. | |
| 5,807,374 A | | 9/1998 | Caizza et al. | |
| 5,833,660 A | | 11/1998 | Nathan et al. | |
| 5,919,169 A | | 7/1999 | Grams et al. | |
| 5,928,202 A | | 7/1999 | Linnebjerg | |
| 5,989,219 A | | 11/1999 | Villas et al. | |
| 6,013,056 A | | 1/2000 | Pettersen | |
| 6,017,325 A | | 1/2000 | Yerfino et al. | |
| 6,053,892 A | | 4/2000 | Meyer | |
| 6,120,479 A | | 9/2000 | Campbell et al. | |
| 6,139,526 A | | 10/2000 | Bedner et al. | |
| 6,217,550 B1 | * | 4/2001 | Capes | 604/110 |
| 6,251,095 B1 | | 6/2001 | Liu | |
| 6,267,749 B1 | | 7/2001 | Miklos et al. | |
| 6,361,525 B2 | * | 3/2002 | Capes et al. | 604/240 |
| 6,607,507 B2 | | 8/2003 | Schottli | |
| 2002/0107489 A1 | | 8/2002 | Lee | |
| 2004/0097884 A1 | * | 5/2004 | Capes et al. | 604/240 |
| 2004/0199113 A1 | | 10/2004 | Capes et al. | |
| 2005/0154353 A1 | | 7/2005 | Alheidt | |
| 2006/0195063 A1 | * | 8/2006 | Lim et al. | 604/110 |

FOREIGN PATENT DOCUMENTS

| | | |
|---|---|---|
| DE | 10159696 A1 | 6/2003 |
| EP | 412968 B1 | 1/1989 |
| EP | 0 364777 | 4/1990 |
| EP | 030804 B1 | 4/1994 |
| FR | 2720649 | 7/1994 |
| GB | 1286690 | 12/1969 |
| GB | 2256146 | 2/1992 |
| GB | 2318060 | 4/1998 |
| GB | 2214082 A | 6/1998 |
| WO | WO 90/03816 | 4/1990 |
| WO | WO 91/12039 * | 8/1991 |
| WO | WO 95/23005 | 8/1995 |
| WO | WO 96/30076 | 10/1996 |
| WO | WO 97/31665 | 9/1997 |
| WO | WO 97/41903 | 11/1997 |
| WO | WO 98/02198 | 1/1998 |
| WO | WO 00/59564 | 10/2000 |
| WO | WO 01/62319 A2 | 8/2001 |
| WO | WO 01/80930 A1 | 11/2001 |
| WO | WO 02/070053 A1 | 9/2002 |
| WO | WO-2004/078243 A2 | 9/2004 |
| WO | WO-2005/032626 A1 | 4/2005 |
| WO | WO-2005/032628 A1 | 4/2005 |
| WO | WO-2005/061030 A1 | 7/2005 |

OTHER PUBLICATIONS

PCT Written Opinion in PCT/US2006/030076, (Feb. 5, 2008), 6 pgs.
PCT International Search Report in PCT/US2006/030050, (Feb. 5, 2008), 7 pgs.
PCT Written Opinion in PCT/US2006/030050, (Feb. 5, 2008), 6 pgs.
Non-Final Office Action in U.S. Appl. No. 11/240,614, mailed Jan. 5, 2010, 13 pgs.
PCT International Search Report in PCT/US03/23756, dated Sep. 17, 2004 and Nov. 10, 2004, 7 pgs.

* cited by examiner

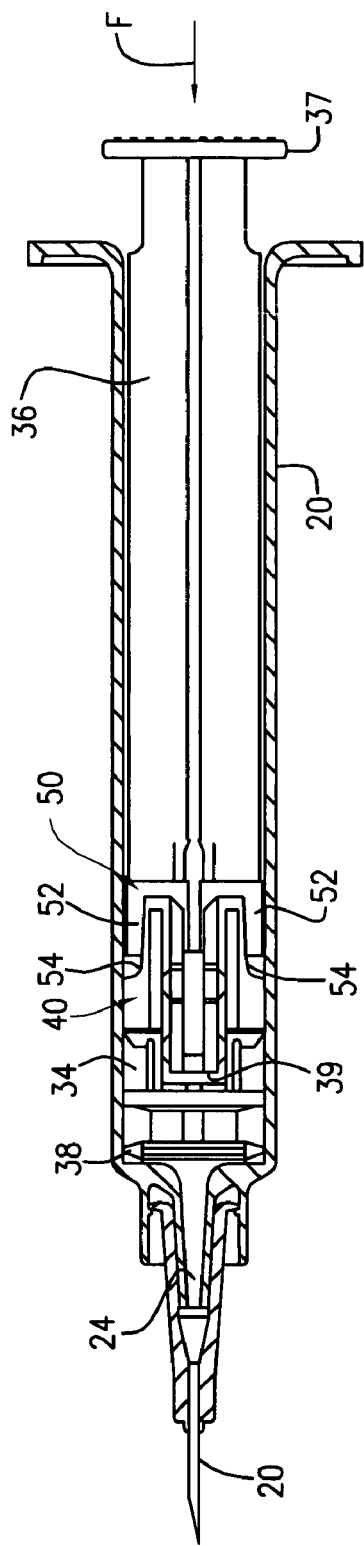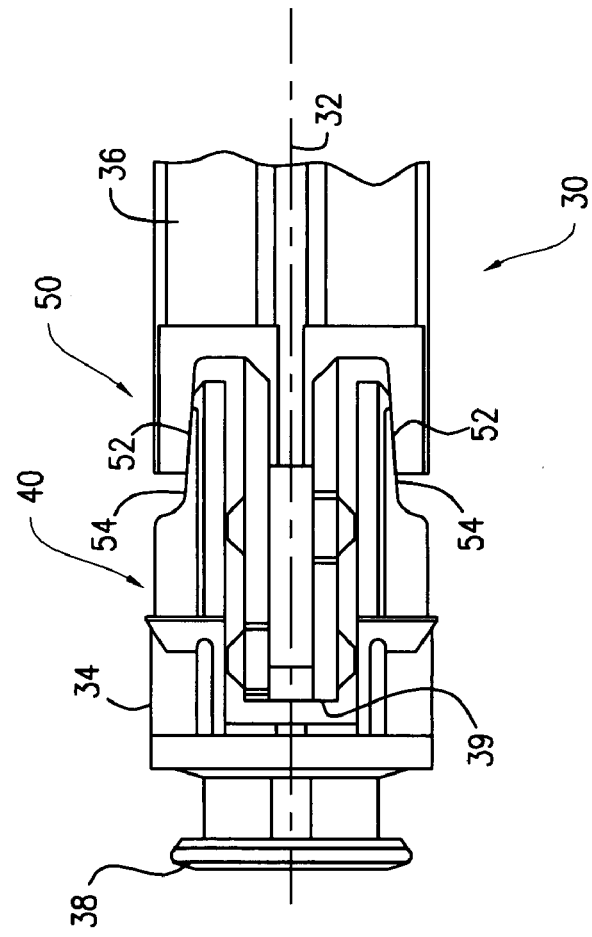
FIG. 6A
FIG. 6B

SINGLE USE SYRINGE

CROSS-REFERENCE TO RELATED APPLICATIONS

This application is a continuation-in-part of U.S. patent application Ser. No. 10/835,848 filed Apr. 30, 2004 which is a continuation of U.S. patent application Ser. No. 10/256,607 filed Sep. 27, 2002, now abandoned, and a continuation-in-part of U.S. patent application Ser. No. 10/706,795 filed Nov. 12, 2003, which is a continuation of U.S. patent application Ser. No. 09/941,030 filed Aug. 28, 2001, now abandoned, which is a continuation of U.S. patent application Ser. No. 09/274,117 filed Mar. 23, 1999 now U.S. Pat. No. 6,361,525, which is a continuation-in-part of U.S. patent application Ser. No. 09/249,431 filed on Feb. 12, 1999, now abandoned, which is a continuation-in-part of U.S. application Ser. No. 09/124,447 filed Jul. 29, 1998, now abandoned.

BACKGROUND

Embodiments of the invention generally relate to impulse-reduction devices on breakable plunger rod assemblies for medical devices, such as syringes.

The re-use of medical equipment that is intended to be single-use is a source of great concern, because such re-use can lead to the transfer of contagious diseases. Syringes comprising a syringe barrel having an elongate tip and a fluid passageway, which is typically the lumen of a needle attached to the syringe through which fluid exits the syringe, are an example of such devices. Such syringes further comprise a plunger having proximal end upon which a user applies force to advance the plunger into the barrel and a proximal end with a distal portion. After use, some amount of fluid typically remains in what is referred to as dead space between the distal portion and the elongate tip of the barrel.

Attempts have been made to prevent the re-use of syringes by providing breakable plunger rods as part of the syringe assembly, examples of which being disclosed in U.S. Pat. No. 6,217,550 (Capes), the entire content of which is incorporated herein by reference and in U.S. patent Publication Number US 2004/0199113 (Capes et al.), the entire content of which is also incorporated herein by reference. Such breakable plunger rod assemblies provide a breakable connection between the main body of the plunger rod and the proximal distal portion. Such breakable connections possess sufficient structural integrity to resist breakage during normal use, but break upon application of additional force. Thus, after injection of the liquid contents of the syringe into a patient or into a suitable container or device such as through the pierceable septum of a catheter connector, a user applies additional force on the thumb press of the plunger rod. This additional force causes the breakable connection to shear, mechanically disconnecting the main body of the plunger rod from the distal portion, and hence disabling further use of the syringe.

After the breakable connection activates (i.e., breaks), the main body of the plunger rod moves forward at a relatively high speed and strikes the distal portion. This creates a contact impulse that compresses the distal portion and forces out fluids that remain within the dead space between the distal portion and the passageway of the elongate tip of the medical device. These fluids can be expelled at high speeds, resulting in a spray from the tip of the opening or lumen if a needle is attached to the syringe. Such a spray poses a risk of spreading contaminating fluids or blood.

It would be therefore desirable to provide syringes and breakable plunger rod assemblies that mitigate the risk of liquids spraying from the nozzle of a medical device when the plunger rod is disabled.

SUMMARY

Embodiments of the invention pertain to a syringe including a barrel and a plunger. The barrel includes a barrel having a fluid chamber, an inside surface, a proximal end, a distal end and a tip extending from the distal end having a passageway in fluid communication with the chamber. In one or more embodiments, the plunger, includes a proximal portion connected by a breakable or collapsible connector to a distal portion. The proximal portion may have a flange upon which a user may push along a longitudinal centerline of the plunger rod. In one or more embodiments, the distal portion has a distal end with a stopper that provides a slidable seal with the inside surface of the barrel for expelling fluids from the passageway. The breakable or collapsible connection breaks or collapses when the force applied by the user exceeds a breaking or collapsing force. In one or more embodiments, an impulse reduction system is disposed between the stopper and the flange to reduce the contact impulse that occurs between the proximal portion and the distal portion when the breakable connection breaks.

In one embodiment, the impulse reduction system comprises a first braking surface that is disposed on the proximal portion, and a second braking surface that is disposed on the distal portion. The braking surfaces are designed to slidingly engage with each other to create a motion-resistive force between the proximal portion and the distal portion. In another embodiment, the first braking surface is sloped with respect to the longitudinal centerline of the plunger rod. In another embodiment, the second braking surface is sloped with respect to the longitudinal centerline of the plunger rod. The surfaces may be roughened to increase the coefficient of friction between the surfaces, and hence the braking force.

In another embodiment, the impulse reduction system comprises an elastic element, such as a spring or similar device, disposed within a gap that separates the proximal portion from the distal portion along the longitudinal centerline.

BRIEF DESCRIPTION OF THE DRAWINGS

FIG. 6A is a side elevational view of the syringe of FIG. 1 illustrated with a force being applied to break the connection between the proximal and distal portions of the plunger rod;

FIG. 6B is a side view of a distal portion of the breakable plunger rod depicted in FIG. 6A after activation;

DETAILED DESCRIPTION

Before describing several exemplary embodiments of the invention, it is to be understood that the invention is not limited to the details of construction or process steps set forth in the following description and drawings. The invention is capable of other embodiments and of being practiced or carried out in various ways.

A convention employed in this application is that the term "proximal" denotes a direction closest to a practitioner, while the term "distal" denotes a direction furthest from the practitioner.

Figure 1:
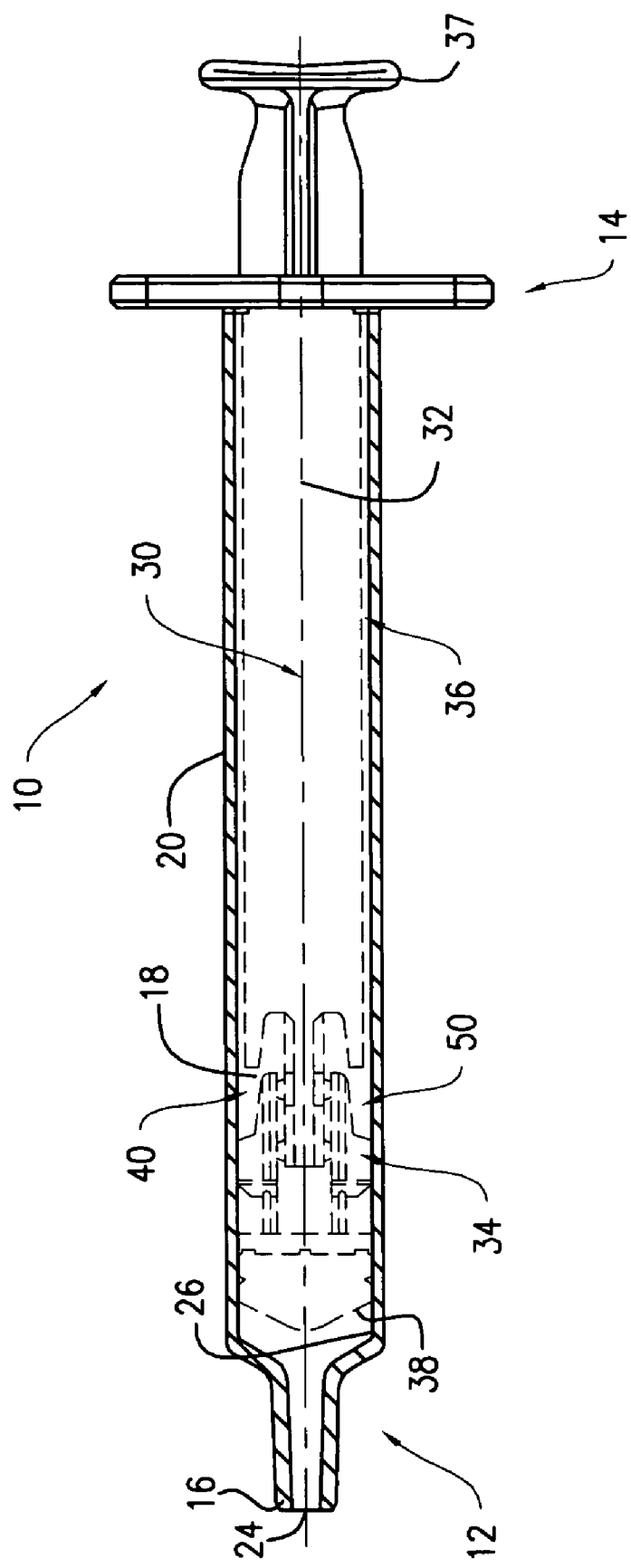
FIG. 1 is a side view of a syringe including a breakable plunger rod disposed within the syringe barrel.
Figure 2:
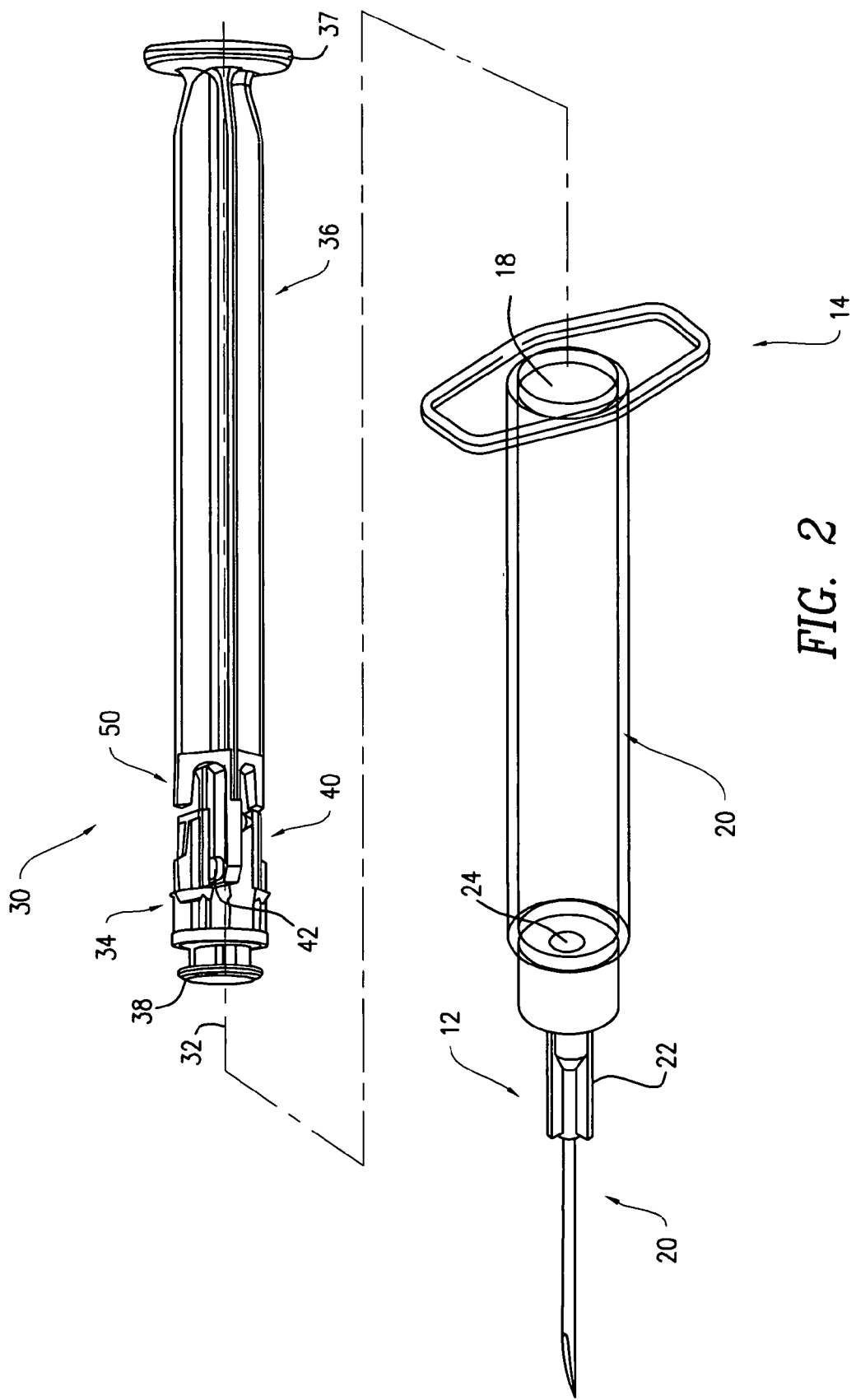
FIG. 2 is an exploded perspective view of the syringe including the breakable plunger rod of FIG. I with a needle and hub attached to the syringe.

According to a one embodiment of the invention depicted in FIGS. 1 and 2, a syringe 10 includes a barrel 20 having an internal surface 26 defining a fluid chamber 18, a distal end 12, a proximal end 14, a distal tip 16, and a breakable or collapsible plunger rod 30. The collapsible plunger rod 30 may be slidably disposed within the barrel 20. The plunger rod 30 includes a distal portion 34, a proximal portion 36 and a stopper 38 connected to the distal portion 34. The distal portion 34 and the proximal portion 36 are connected to each other via collapsible or breakable connection 40. The stopper 38 is slidably positioned in fluid tight engagement with the internal surface 26, and is able to slide distally and proximally along longitudinal centerline 32. By moving the plunger rod distally, the stopper 38 may force fluids out of fluid passage way or opening 24 in the distal tip 16. By moving proximally, the stopper 38 may draw fluids through the fluid passageway 24 and into the fluid chamber 18. It will be appreciated by those skilled in the art that the distal tip 16 of the syringe 10 may be releasably or permanently connected to a needle assembly via a hub 22 as is known in the art. Such needle assemblies include, but are not limited to, Luer lock type needle assemblies and Luer slip type needle assemblies. It is further within the purview of this invention to include a needle assembly having a one piece construction wherein the cannula and the hub are formed of one piece.

A proximal end of the proximal portion 36 may include a thumb flange 37 that a user may push to move the plunger rod 30 and stopper 38 distally, or pull upon to move the plunger rod 30 and stopper 38 proximally. An impulse reduction system 50 is disposed on the plunger rod 30 between the stopper 38 and the flange 37 to reduce the contact impulse between the proximal portion 36 and the distal portion 34 generated when the breakable connection 40 breaks. Although FIGS. 1 and 2 show an impulse reduction system 50 that utilizes friction surfaces, it will be appreciated that any suitable impulse reduction system 50 may be utilized within the syringe 10.

Figure 3:
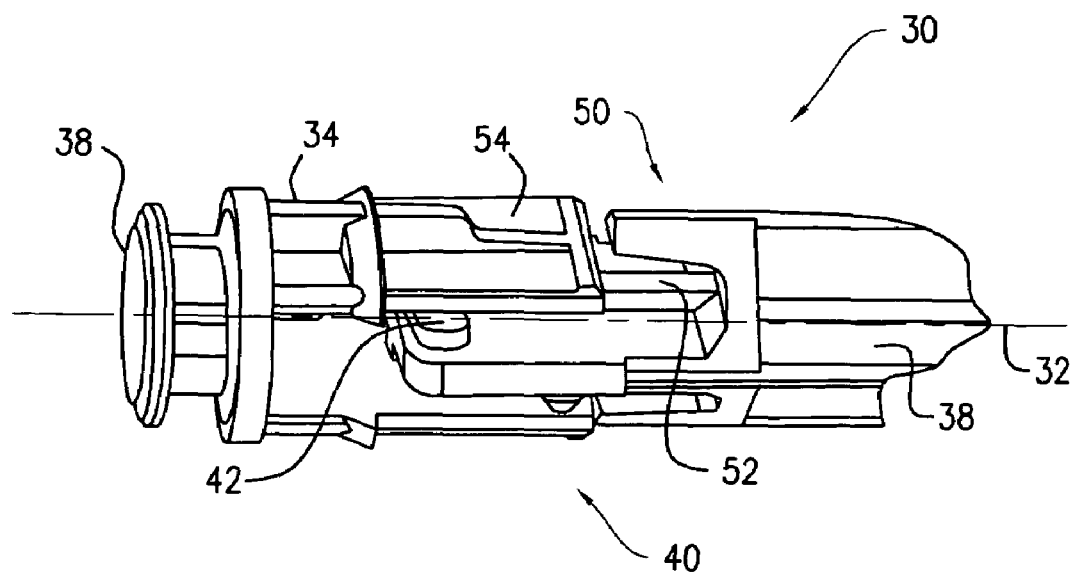
FIG. 3 is a perspective view of a distal portion of the breakable plunger rod depicted in FIG. 1 prior to activation.
Figure 4:
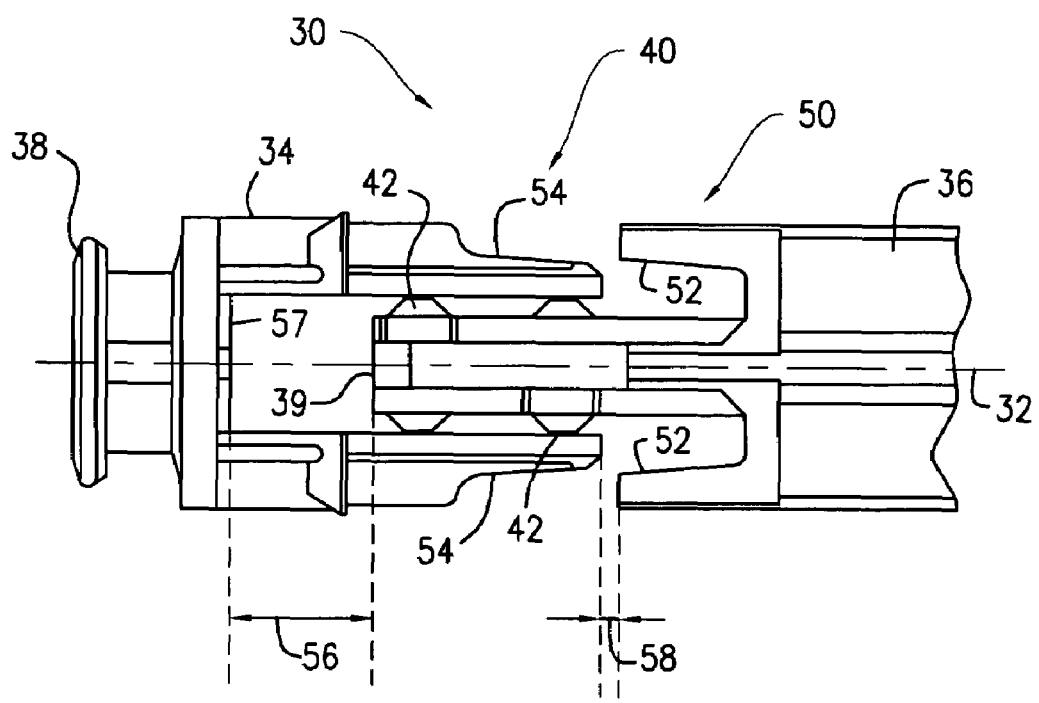
FIG. 4 is a side view of a distal portion of the breakable plunger rod depicted in FIG. 1 prior to activation.
Figure 5:
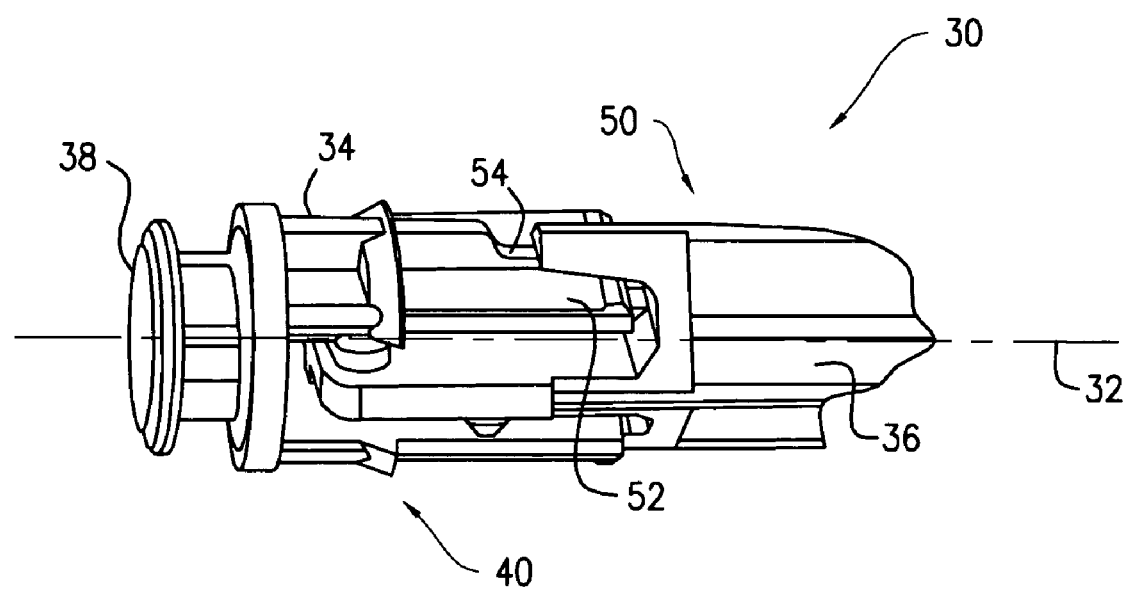
FIG. 5 is a perspective view of a distal portion of the breakable plunger rod depicted in FIG. 1 after activation.

As shown in FIGS. 2-6, the breakable connection 40 may include protuberances 42 that are transverse to the longitudinal centerline 32, and which connect overlapping regions of the proximal portion 36 with corresponding regions on the distal portion 34. FIGS. 3 and 4 show the collapsible plunger rod 30 prior to the breakable connection 40 breaking. FIGS. 5 and 6A-6B show the collapsible plunger rod 30 after the breakable connection 40 has been activated. The protuberances 42 are manufactured to withstand typical-use shear forces generated when a user draws fluids into fluid passageway 24, or expels them through opening 24 during normal use in medical procedures. However, upon the application of a certain breaking force indicated by arrow F in FIG. 6A, which should not be so small as to risk unintentional activation of breakable connection 40 during application of force during normal use, nor too great as to place undue strain on the user, the breakable connection 40 activates. That is, when a user presses down upon thumb flange 37 with the intent to disable the syringe 10 using an additional force, the protuberances 42 shear away from distal portion 34. Thus, the breaking force is the total force that includes the force applied under normal use plus some additional force required to break the breakable connection. As a result, proximal portion 36 mechanically disconnects from distal portion 34, collapsing the plunger rod, effectively disabling distal portion 34 and thus rendering syringe 10 unusable.

The breaking force depends on various dimensions of the syringe barrel and plunger, the viscosity of the liquid being delivered and the mechanical and hydraulic forces encountered by the filling and delivery process. If the breakable connection is too weak, the proximal and distal portions will separate during normal use of the syringe and if the force required to break the breakable connection is too high the user may not be able to easily break the breakable connection as intended. The skilled artisan can select the appropriate materials and/or connections to provide the proper breaking force to cause the connection to break and the plunger rod to collapse for a particular syringe design and/or use.

To prevent spraying from fluid passageway 24 or lumen of a needle attached to the syringe that would otherwise result from most distal end 39 of proximal portion 36 impacting distal portion 34 after activation of breakable connection 40, plunger rod 30 is provided an impulse reduction system 50. As shown in FIGS. 2-6, one or more first braking surfaces 52 may be provided on the proximal portion 36, which may be located within the distal region of the proximal portion 36. The first braking surface 52 may be slightly sloped with respect to the longitudinal centerline 32 so that the first braking surface 52 becomes more distant from the longitudinal centerline 32 along the distal direction. The first braking surface 52 may define a relatively rough finish to increase the coefficient of friction of the first surface 52. The distal portion 34 is provided one or more corresponding second braking surfaces 54, which are aligned with the first braking surfaces 52, and which may be provided within the proximal region of the distal portion 34. The second braking surfaces 54 may also define roughened surfaces to increase their coefficients of friction. The braking surfaces 52, 54 may be located adjacent to the breakable connection 40.

As shown in FIGS. 5 and 6, when the breakable connection 40 activates, the proximal portion 36 moves along the longitudinal centerline 32 with respect to the distal portion 34. There thus exists, immediately after activation of breakable connection 40, relative motion between the proximal portion 36 and distal portion 34, which brings the braking surfaces 52, 54 into contact with each other. The first braking surface 52 thus slides against the second braking surface 54. The friction developed between the first braking surface 52 and the second braking surface 54 creates a motion-resistive force between the proximal portion 36 and distal portion 34. The wedge-shaped alignment of the first braking surface 52 and the second braking surface 54 with respect to the longitudinal centerline 32 causes the motion-resistive force to increase as a function of distal movement of the proximal portion 36 along the longitudinal centerline 32 with respect to the distal portion 34. This motion-resistive force tends to slow the relative motion between the proximal portion 36 and the distal portion 34, and hence acts as a shock absorber that reduces contact impulse between the proximal portion 36 and distal portion 34.

It will be appreciated that, prior to activation of the breakable connection 40, a gap 56, which will be called the contact gap, exists between the proximal portion 36 and distal portion 34 through which the proximal portion 36 travels after activation of the breakable connection 40. Absent any sort of impulse-reduction system 50, when this contact gap closes, contact between the respective surfaces that composed the contact gap leads to an impulse that compresses stopper 38, and which thus leads to a sharp ejection of material from fluid passageway 24. The exact location of this contact gap, and its width along the longitudinal centerline 32, will depend upon the specific geometric configurations of the proximal portion 36 and distal portion 34. For the embodiment depicted in FIGS. 2-6, and with specific reference to FIG. 4, the contact gap 56 extends from the most distal end 39 of proximal portion 36 along the longitudinal centerline 32 to surface 57 on the distal portion 34. The width, as measured along longitudinal centerline 32, of contact gap 56 may be greater than the gap 58, also measured along longitudinal centerline 32, that separates the most distal end of first braking surface 52 from the most proximal end of second braking surface 54 prior to activation of the breakable connection 40. As a result, the impulse reduction system 50 has ample distance along the longitudinal centerline 32 to develop a braking force that slows the relative movement between the proximal portion 36 and the distal portion 34, and which thus reduces the contact impulse between the proximal portion 36 and distal portion 34 to reduce spraying of fluids from the fluid passageway 24.

Other types of shock-absorbing mechanisms may be utilized to reduce the impulse developed between the proximal portion and distal portion. For example, an elastic element may be disposed within a gap separating the proximal portion from the distal portion. As the elastic element is compressed by the proximal portion, the elastic element reduces the speed of relative motion between the proximal portion and distal portion, and thereby reduces the contact impulse between the proximal portion and the distal portion.

Figure 7:
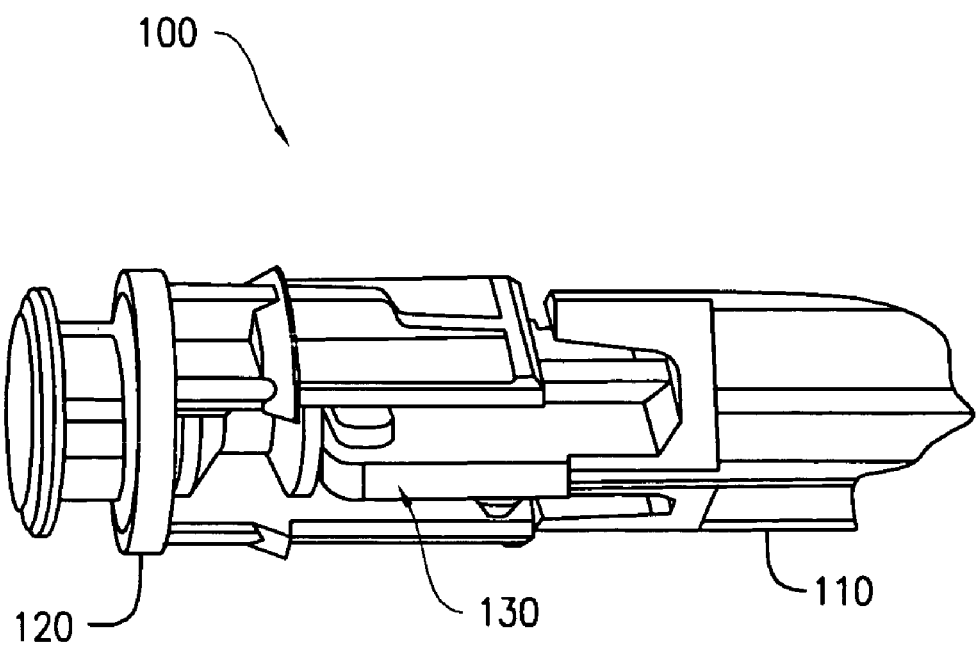
FIG. 7 is a perspective view of a distal portion of another breakable plunger rod.
Figure 8:
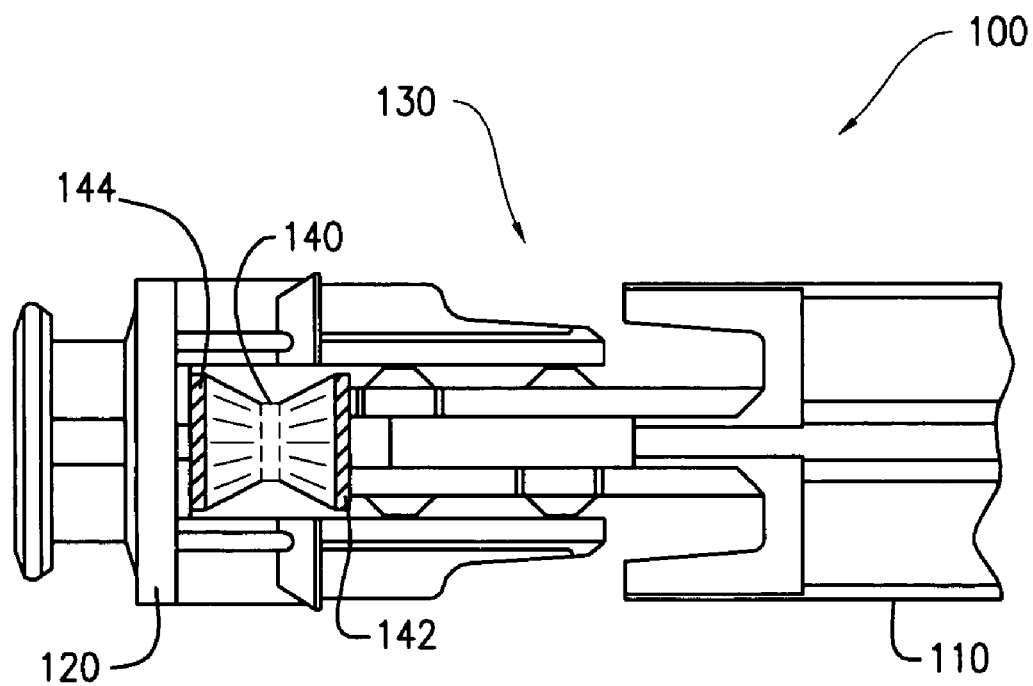
FIG. 8 is a side view of the breakable plunger rod shown in FIG. 7.

An embodiment utilizing an elastic element is depicted in FIGS. 7 and 8. A collapsible plunger rod 100 is similar to the collapsible plunger rod 30 discussed above, having a proximal portion 110 connected to a distal portion 120 by way of a breakable connection 130. A compressible elastic element 140 is disposed in a gap between the proximal portion 110 and the distal portion 120. Specifically, the elastic element 140 is disposed adjacent to the breakable connection 130, and just forward of the breakable connection in the distal direction. When the breakable connection 130 shears from the distal portion 120, the proximal portion 110 begins to advance in the distal direction. As the proximal portion 110 advances, it compresses a first arm 142 of the elastic element towards a second arm 144 of the elastic element. The elastic element 140 creates a force that resists this compression, and which thus slows the forward velocity of the proximal portion 110. The elastic element 140 thus acts as a shock absorber that reduces the shock associated with the activation of the breakable connection 130, and which thus reduces the contact impulse of the proximal portion 110 impacting the distal portion 120.

Figure 9:
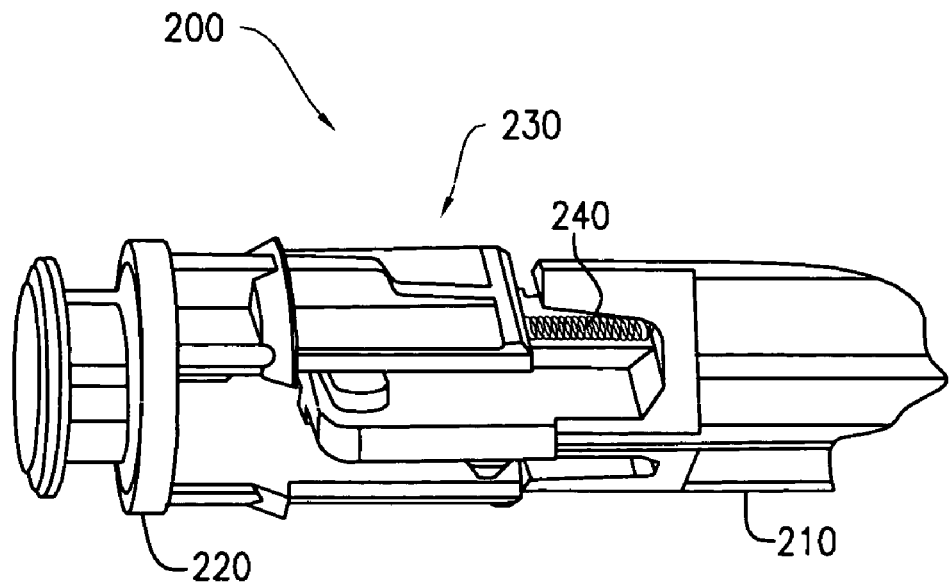
FIG. 9 is a perspective view of a distal portion of yet another breakable plunger rod.
Figure 10:
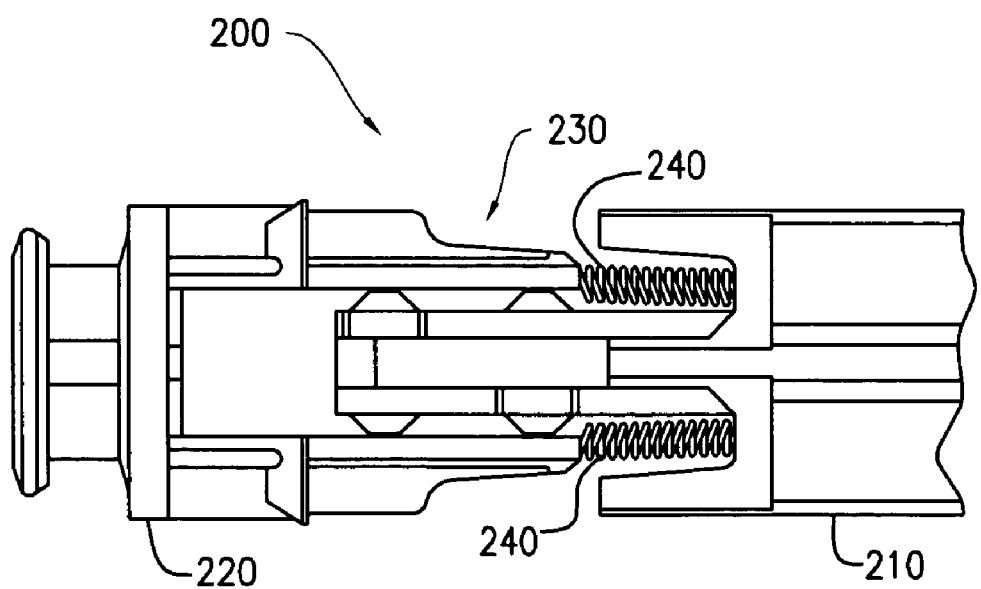
FIG. 10 is a side view of the breakable plunger rod shown in FIG. 9.

An alternative embodiment utilizing elastic elements as shock absorbers is depicted in FIGS. 9 and 10. A collapsible plunger rod 200 utilizes springs 240 disposed in gaps between proximal portion 210 and distal portion 220 to reduce the contact impulse of the proximal portion 210 striking the distal portion 220 when the breakable connection 230 activates. In particular, the springs 240 may be disposed proximally adjacent to the breakable connection 230. Of course, for both embodiments depicted in FIGS. 7-8 and 9-10, any suitable elastic device or devices may be used to slow the relative motion between the proximal portion and the distal portion.

It is within the purview of the present invention to include plunger rods and stoppers which are separately formed or integrally formed of the same material or different materials such as in two-color molding, or separately formed of the same or different materials and joined together by mechanical means, adhesives, ultrasonic welding, heat sealing or other suitable means. Stoppers are preferably made of elastomeric material such as natural rubber, synthetic rubber, thermoplastic elastomers and combinations thereof. It is understood that the plunger of the present embodiment merely illustrates these many possibilities.

In use, the syringe of this embodiment can be filled from a vial, ampoule or other suitable container using known safe procedures. According to embodiments of the invention, the plunger can be moved back and forth along the barrel as many times as necessary to properly fill the syringe barrel. For example, the syringe barrel may be filled with sterile water and then the sterile water can be injected into a vial containing a lyophilized medication which is then drawn back into the syringe barrel. Many single-use syringes in the prior art only allow one proximal motion of the plunger with respect to the barrel. With these single-use syringes, once the plunger is moved in a distal direction with respect to the barrel it can no longer be withdrawn. Therefore, mixing sterile water and a lyophilized medication as described above is not possible.

While the foregoing is directed to embodiments of the present invention, other and further embodiments of the invention may be devised without departing from the basic scope thereof, and the scope thereof is determined by the claims that follow.

What is claimed is:

1. A syringe comprising:
   a barrel including an interior surface, a proximal end, a distal end, a fluid chamber and a tip at the distal end including an opening to allow fluid to pass therethrough;
   a plunger rod including a proximal portion having a proximal end with a flange adapted to accept a force applied from a user along a longitudinal centerline of the plunger rod and a distal end; a distal portion having a distal end with a stopper adapted to provide a slidable seal with the interior surface of the barrel; a breakable connection between the proximal portion and the distal portion adapted to break when the force applied by the user exceeds a breaking force, wherein the breaking force is greater than a force needed to expel fluid through the syringe tip during normal use; and
   means for reducing a contact impulse between the proximal and distal portions of the plunger rod when the breakable connection is broken, the means comprising a first surface on the plunger rod which contacts a second surface after breaking of the breakable connection, thereby reducing impact of the distal end of the proximal portion on the distal portion.

2. The syringe of claim 1 wherein the means for reducing the contact impulse comprises:
   a first braking surface disposed on the proximal portion; and
   a second braking surface disposed on the distal portion, the second braking surface adapted to slidingly engage with the first braking surface to create a motion-resistive force between the proximal portion and the distal portion.

3. The syringe of claim 2 wherein the first braking surface is sloped with respect to the longitudinal centerline of the plunger rod.

4. The plunger rod of claim 2 wherein the second braking surface is sloped with respect to the longitudinal centerline of the plunger rod.

5. The syringe of claim 3 wherein a first distance along the longitudinal centerline of the plunger rod separating a distal end of the proximal portion from the distal portion exceeds a second distance separating a most distal portion of the first braking surface from a most proximal portion of the second braking surface.

6. The syringe of claim 2 wherein the first braking surface is disposed along a distal region of the proximal portion, and the second braking surface is disposed along a proximal region of the distal portion.

7. The syringe of claim 5 wherein the first braking surface or the second braking surface is disposed adjacent to the breakable connection.

8. The syringe of claim 1 wherein the means for reducing the contact impulse comprises an elastic element disposed within a gap along the longitudinal centerline that separates the proximal portion from the distal portion.

9. The syringe of claim 8 wherein the elastic element is disposed adjacent to the breakable connection.

10. The syringe of claim 9 wherein the elastic element is disposed distally adjacent to the breakable connection.

11. The syringe of claim 10 wherein the elastic element includes a first arm adapted to compress into a second arm in response to the breakable connection breaking.

12. The syringe of claim 9 wherein the elastic element is disposed proximally adjacent to the breakable connection.

13. The syringe of claim 8 wherein the elastic element includes one or more springs.

* * * * *